Nov. 29, 1949. A. KREBS Plant Pat. 902
DWARF POLYANTHA ROSE PLANT
Filed Dec. 23, 1947
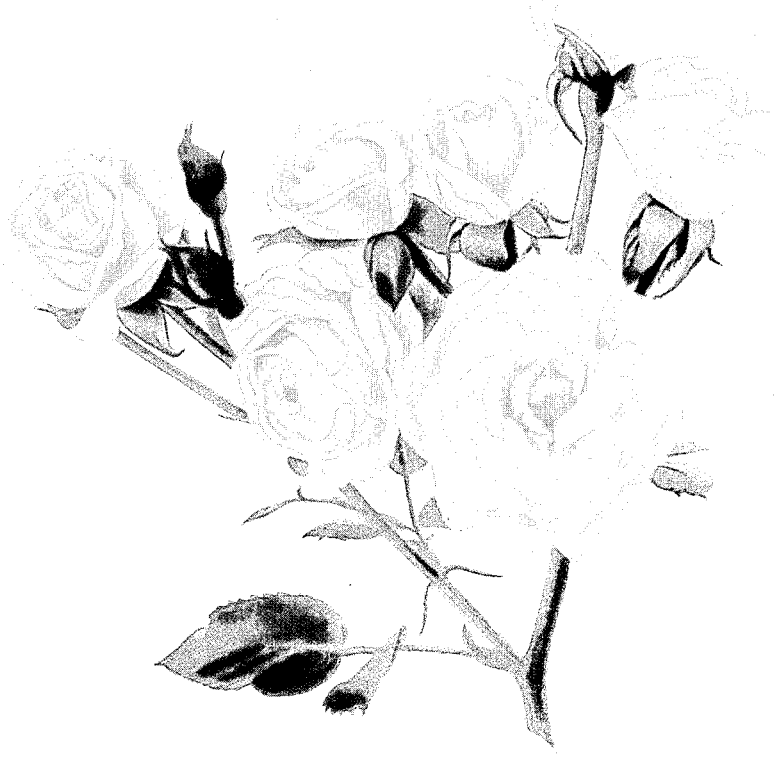
INVENTOR
Alfred Krebs
By Orville M. Kile
Plant Pat. Agt.

Patented Nov. 29, 1949

Plant Pat. 902

UNITED STATES PATENT OFFICE

902

DWARF POLYANTHA ROSE PLANT

Alfred Krebs, Montebello, Calif., assignor to Howard & Smith, Montebello, Calif.

Application December 23, 1947, Serial No. 793,351

1 Claim. (Cl. 47—61)

My present invention relates to improvements in rose plants of the polyantha type. It resulted from a cross made by me, of two unnamed seedlings of which one of the earlier progenitors was the Mme. Cecile Brunner. It produces a flower of pure soft pink with petals in rosette form.

The form of the plant is dwarf and compact and is heavily foliaged right down to the base, making it excellent for use as a pot plant especially since tests under glass have demonstrated it to be a good forcing rose. The flowers are excellent for use in corsages.

This new variety has been asexually reproduced from cuttings, in the greenhouses of Howard & Smith at Montebello, California, and its characteristics appear to be permanent.

Accompanying illustrations show a cluster or truss of buds and flowers in approximately their true colors.

Following is a detailed description of this new rose variety. Color nomenclature refers to the ordinary dictionary meaning of the term except where plate references are given.

*The plant*

Growth habit and form: Dwarf and compact. Well-foliaged right to base of plant for entire season.

Blooming habit: Remontant throughout the season in the open and throughout the year when grown under glass at 60-degree temperatures.

Stems:

*Color.*—Medium green.
*Strength.*—Very strong.
*Rigidity.*—Stiff and rigid. Stems hold trusses in erect position.
*Surface.*—Very smooth.
*Thorns.*—Very few and when manifest, only at base of plant.

Foliage:

*Leaflets.*—3 to 5.
*Quantity.*—Heavily foliaged right down to the ground. When used as a pot plant, the pot is practically hidden.
*Shape.*—Oval, with acute apex. Edge crenate.
*Size.*—Total leaf averages 3½ inches long by 2½ inches wide. Terminal leaflet approximately 1½ by ¾ inch.
*Texture.*—Very leathery.
*Color.*—Dark green.
*Leaf stem.*—Medium in length. Slightly lighter than leaf.
*Stipules.*—Basal, smooth, ¼ to $\frac{1}{16}$ inch wide.

*The flower*

Bud:

*Size.*—Small, averaging ¾ inch long.

*Shape.*—Ovoid, with outer petals slightly reflexed at edges.
*Color.*—Uniform pure soft pink (fully opened flower slightly darker than Deep Rose Pink, Plate XII, Ridgway's Color Standards and Nomenclature, with others much darker and brighter).
*Opening.*—Slow.
*Peduncle.*—Short, straight, rigid, same color as stems, usually 1½ to 2 inches long.

Bloom:

*Borne.*—In clusters, on many-branched stems.
*Size.*—Averages 2¼ inches in diameter.
*Form.*—Close rosette, opening into camellia-like form with petals evenly superimposed. In fully opened flower, petals reflex slightly at edges.
*Color.*—Same as bud.
*Discoloration.*—None.
*Petalage.*—Average 40 to 45 petals.
*Fragrance.*—Very slight.
*Longevity.*—Excellent. Blooms either cut or on plant last a full week to ten days.

Petals:

*Shape.*—Nearly circular. Slightly wavy at tip.
*Aspect.*—Silky.
*Size.*—Average 1 inch by $1\frac{1}{16}$ inches.
*Color.*—Uniform deep clear pink.
*Arrangement.*—Compact. Uniformly disposed in camellia-like form.
*Texture.*—Very substantial.
*Persistence.*—Very lasting, finally dropping off cleanly.

Reproductive organs:

*Pistils.*—Light green. Invisible in open rose.
*Stamens.*—Few. Filaments pale green. Anthers light brown. Pollen yellow.
*Ovaries.*—White. Imperfect.
*Fruit.*—None.

Having thus disclosed my invention, I claim:

The new and distinct variety of polyantha rose plant, substantially as herein shown and described, characterized particularly by its dwarf, compact and well-branched growth; its abundant leathery foliage to base of plant; the almost complete absence of thorns from its stems; its abundantly remontant blooming habit; its ovoid buds opening into camellia-like form when flowers are fully developed; the rich pink color and large number of petals of its buds and flowers; and the longevity of its flowers either cut or on the bush.

ALFRED KREBS.

No references cited.